(12) United States Patent
Chakraborty et al.

(10) Patent No.: US 9,944,943 B2
(45) Date of Patent: Apr. 17, 2018

(54) METHOD OF PRODUCING STRESS TOLERANT PLANTS OVEREXPRESSING CASUN1

(71) Applicant: National Institute of Plant Genome Research, New Delhi (IN)

(72) Inventors: Niranjan Chakraborty, New Delhi (IN); Subhra Chakraborty, New Delhi (IN); Dinesh Kumar Jaiswal, New Delhi (IN); Poonam Mishra, New Delhi (IN); Pratigya Subba, New Delhi (IN); Divya Rathi, New Delhi (IN)

(73) Assignee: National Institute of Plant Genome Research, New Delhi (IN)

( * ) Notice: Subject to any disclaimer, the term of this patent is extended or adjusted under 35 U.S.C. 154(b) by 560 days.

(21) Appl. No.: 14/588,737

(22) Filed: Jan. 2, 2015

(65) Prior Publication Data

US 2015/0184190 A1    Jul. 2, 2015

(30) Foreign Application Priority Data

Jan. 2, 2014    (IN) .................................. 8/DEL/2014

(51) Int. Cl.
C12N 15/82    (2006.01)
C07K 14/415    (2006.01)

(52) U.S. Cl.
CPC ........ *C12N 15/8273* (2013.01); *C07K 14/415* (2013.01); *C12N 15/8271* (2013.01)

(58) Field of Classification Search
CPC ............ C12N 15/8241; C12N 15/8271; C12N 15/8273; C12N 15/8261
See application file for complete search history.

(56) References Cited

U.S. PATENT DOCUMENTS

2008/0295196 A1*  11/2008  Abad .................... C07K 14/415
                                                      800/275

OTHER PUBLICATIONS

Graumann, Katja, and David E. Evans. "Plant SUN domain proteins: components of putative plant LINC complexes?." Plant signaling & behavior 5.2 (2010): 154-156.*
Fujita, Miki, et al. "Crosstalk between abiotic and biotic stress responses: a current view from the points of convergence in the stress signaling networks." Current opinion in plant biology 9.4 (2006): 436-442.*
Davletova, Sholpan, et al. "The zinc-finger protein Zat12 plays a central role in reactive oxygen and abiotic stress signaling in *Arabidopsis*." Plant physiology 139.2 (2005): 847-856.*
Abdalla et al., "Analysis of the nuclear proteome of the resurrection plant *Xerophyta viscosa* in response to dehydration stress using iTRAQ with 2DLC and tandem mass spectrometry," *Journal of Proteomics* 75:2361-2374, 2012.

Abi-Ghanem et al., "Nitrogen Fixation by US and Middle Eastern Chickpeas with Commercial and Wild Middle Eastern Inocula," *ISRN Soil Science* Article 2012; 5 pages.
Afzal et al., "Plant Receptor-Like Serine Threonine Kinases: Roles in Signaling and Plant Defense," *MPMI* 21(5): 507-517, 2008.
Almén et al., "Mapping the human membrane proteome: a majority of the human membrane proteins can be classified according to function and evolutionary origin," *BMC Biology* 7(50): 1-14, 2009.
Alvim et al., "Enhanced Accumulation of BiP in Transgenic Plants Confers Tolerance to Water Stress1," *Plant Physiol.* 126:1-13, 2001.
Andaluz et al., "Proteomic profiles of thylakoid membranes and changes in response to iron deficiency," *Photosynth Res* 89:141-155, 2006.
Baginsky et al., "*Arabidopsis thaliana* proteomics: from proteome to genome," *Journal of Experimental Botany* 57(7):1485-1491, 2006.
Barkla et al., "Quantitative Proteomics of the Tonoplast Reveals a Role for Glycolytic Enzymes in Salt Tolerance," *The Plant Cell* 21:4044-4058, Dec. 2009.
Bhushan et al., "Comparative Proteomics Analysis of Differentially Expressed Proteins in Chickpea Extracellular Matrix during Dehydration Stress," *Molecular & Cellular Proteomics* 6: 1868-1884, 2007.
Bhushan et al., "Dehydration-Responsive Reversible and Irreversible Changes in the Extracellular Matrix: Comparative Proteomics of Chickpea Genotypes with Contrasting Tolerance," *Journal of Proteome Research* 10:2027-2046, 2011.
Casey et al., "Proteomic Analysis Reveals Different Protein Changes during Endothelin-1- or Leukemic Inhibitory Factory-induced Hypertrophy of Cardiomyocytes in Vitro," *Molecular & Cellular Proteomics* 4(5):651-661, 2005.
Clarke et al., "Roles of Salicylic Acid, Jasmonic Acid, and Ethylene in cpr-Induced Resistance in *Arabidopsis*," *The Plant Cell* 12:2175-2190, Nov. 2000.
Clough et al., "Floral dip: a simplified method for *Agrobacterium*-mediated transformation of *Arabidopsis thaliana*," *The Plant Journal* 16(6):735-743, 1998.
DiDonato et al., "Mapping of the Inducible Iκb Phosphorylation Sites That Signal Its Ubiquitination and Degradation," *Molecular and Cellular Biology* 16(4):1295-1304, Apr. 1996.
Dumas-Gaudot el al., "A technical trick for studying proteomics in parallel to transcriptomics in symbiotic root-fungus interactions," *Proteomics* 4:451-453, 2004.
Friederichs et al., "Genetic Analysis of Mps3 SUN Domain Mutants in *Saccharomyces cerevisiae* Reveals an Interaction with the SUN-Like Protein Slp1," *G3 Genes, Genomes, Genetics* 2:1703-1719, Dec. 2012.
Fukao et al., "iTRAQ Analysis Reveals Mechanisms of Growth Defects Due to Excess Zinc in *Arabidopsis*," *Plant Physiology* 155:1893-1907, 2011.

(Continued)

*Primary Examiner* — Lee A Visone
*Assistant Examiner* — Weihua Fan
(74) *Attorney, Agent, or Firm* — Seed IP Law Group LLP

(57) ABSTRACT

The present disclosure relates to a method of producing transgenic plants that over-express the chickpea protein, CaSUN1, expression of which enhances the stress tolerance of the transgenic plants. The disclosure further provides recombinant DNA constructs, recombinant DNA vectors, and recombinant host cells comprising the cDNA encoding CaSUN1.

16 Claims, 8 Drawing Sheets
(1 of 8 Drawing Sheet(s) Filed in Color)

(56) References Cited

OTHER PUBLICATIONS

Good et al., "The effects of drought stress on free amino acid accumulation and protein synthesis in *Brassica napus,*" *Physiologic Plantarium* 90:9-14, 1994.
Graumann et al., "Characterization of SUN-domain proteins at the higher plant nuclear envelope," *The Plant Journal* 61:134-144, 2010.
Graumann et al., "Nuclear envelope dynamics during plant cell division suggest common mechanisms between kingdoms," *Biochem. J.* 435:661-667, 2011.
Heijne, "Membrane-protein topology," *Molecular Cell Biology* 7:909-919, Dec. 2006.
Irons et al., "The first 238 amino acids of the human lamin B receptor are targeted to the nuclear envelope in plants," *Journal of Experimental Botany* 54(384):943-950, Mar. 2003.
Irsigler et al., "Expression profiling on soybean leaves reveals integration of ER and osmotic-stress pathways," *BMC Genomics* 8(431):Nov. 1-15, 2007.
Ishihama et al., "Exponentially Modified Protein Abundance Index (emPAI) for Estimation of Absolute Protein Amount in Proteomics by the Number of Sequenced Peptides per Protein," *Molecular & Cellular Proteomics* 4.9:1265-1272, 2005.
Jaiswal et al., "Proteomic analysis reveals the diversity and complexity of membrane proteins in chickpea (*Cicer arietinum* L.)," *Proteome Science* 10(59):1-16, 2012.
Jonikas et al., "Comprehensive Characterization of Genes Required for Protein Folding in the Endoplasmic Reticulum," *Science* 323:1693-1697, Mar. 2009.
Kemp et al., "Suppressors of zyg-1 Define Regulators of Centrosome Duplication and Nuclear Association in *Caenorhabditis elegans,*" *Genetics* 176:95-113, May 2007.
Kim et al., "Molecular Chaperone Functions in Protein Folding and Proteostasis," *Annu. Rev. Biochem.* 82:323-355, 2013.
Kohno, "Stress-sensing mechanisms in the unfolded protein response: similarities and differences between yeast and mammals," *J. Biochem.*147(1):27-33, 2010.
Koiwa et al., "The STT3a Subunit Isoform of the *Arabidopsis* Oligosaccharyltransferase Controls Adaptive Responses to Salt/Osmotic Stress," *The Plant Cell* 15:2273-2284, Oct. 2003.
Konishi et al., "Characterization of Vacuolar Membrane Proteins Changed in Rice Root Treated with Gibberellin," *Journal of Proteome Research* 4:1775-1780, 2005.
Kota et al., "Advances in qualitative and quantitative plant membrane proteomics," *Phytochemistry* 72:1040-1060, 2011.
Krasensky et al., "Drought, salt, and temperature stress-induced metabolic rearrangements and regulatory networks," *Journal of Experimental Botany* 63(4):1593-1608, 2012.
Kurepa et al., "Proteasome regulation, plant growth and stress tolerance," *Plant Signaling & Behavior* 4(10):924-927, Oct. 2009.
Lawlor, "Genetic engineering to improve plant performance under drought: physiological evaluation of achievements, limitations, and possibilities," *Journal of Experimental Botany* 64(1):83-108, 2013.
Lu et al., "Interaction between Aldolase and Vacuolar $H^7$-ATPase," *The Journal of Biological Chemistry* 276(32):30407-30413, 2001.
Malone et al., "UNC-84 localizes to the nuclear envelope and is required for nuclear migration and anchoring during *C. elegans* development," *Development* 126:3171-3181, 1999.
Mans et al., "Comparative Genomics, Evolution and Origins of the Nuclear Envelope and Nuclear Pore Complex," *Cell Cycle* 3(12):1625-1650, Oct. 2004.

Martin et al., "Lipid microdomains—plant membranes get organized," *TRENDS in Plant Science* 10(6):263-265, Jun. 2005.
Matsui et al., "*Arabidopsis* Transcriptome Analysis under Drought, Cold, High-Salinity and ABA Treatment Conditions using a Tiling Array," *Plant Cell Physiol.* 49(8):1135-1149, 2008.
Murphy et al., "Structure and expression of the maize (*Zea mays* L.) SUN-domain protein gene family: evidence for the existence of two divergent classes of SUN proteins in plants," *BMC Plant Biology* 10(269):1-22, 2010.
Murphy et al., "The maize (*Zea mays*) desynaptic (dy) mutation defines a pathway for meiotic chromosome segregation, linking nuclear morphology, telomere distribution and synapsis," *Journal of Cell Science* 125:3681-3690, 2012.
Neupert et al., "Translocation of Proteins into Mitochondria," *Annu. Rev. Biochem* 76:723-749, 2007.
Oda et al., "Dynamics of *Arabidopsis* SUN proteins during mitosis and their involvement in nuclear shaping," *The Plant Journal* 66:629-641, 2011.
Pang et al., "Comparative Proteomics of Salt Tolerance in *Arabidopsis thaliana* and *Thellungiella halophile,*" *Journal of Proteome Research* 9:2584-2599, 2010.
Parsell et al., "The Function of Heat-Shock Proteins in Stress Tolerance: Degradation and Reactivation of Damaged Proteins," *Annu. Rev. Genet.* 27:437-496, 1993.
Saibil, "Chaperone machines for protein folding, unfolding and disaggregation," *Nature Reviews Molecular Cell Biology AOP1*:1-13, Sep. 12, 2013.
Shinozaki et al., "Gene networks involved in drought stress response and tolerance," *Journal of Experimental Botany* 58(2):221-227, 2007.
Starr, "A nuclear-envelope bridge positions nuclei and moves chromosomes," *Journal of Cell Science* 122:577-586, 2009.
Süss et al., "Calvin cycle multienzyme complexes are bound to chloroplast thylakoid membranes of higher plants in situ," *Pro. Natl. Acad. Sci.* USA 90:5514-5518, Jun. 1993.
Tamura et al., "MEGA5: Molecular Evolutionary Genetics Analysis Using Maximum Likelihood, Evolutionary Distance, and Maximum Parsimony Methods," *Mol. Biol. Evol.* 28(10):2731-2739, 2011.
Uhrig, "Protein interaction networks in plants," *Planta* 224:771-781, 2006.
Utsunomiya et al., "Carbonic anhydrase in the plasma membranes from leaves of $C_3$ and $C_4$ plants," *Physiologia Plantarum* 88:413-419, 1993.
Valledor et al., "Back to the basics: Maximizing the information obtained by quantitative two dimensional gel electrophoresis analyses by an appropriate experimental design and statistical analyses," *Journal of Proteomics* 74:1-18, 2011.
Varshney et al., "Draft genome sequence of chickpea (*Cicer arietinum*) provides a resource for trait improvement," *Nature Biotechnology* 31(3):241-248, Mar. 2013.
Wang et al., "Mechanotransduction at a distance: mechanically coupling the extracellular matrix with the nucleus," *Molecular Cell Biology* 10:75-82, Jan. 2009.
Wilson III et al., "Trans-complementation by human apurinic endonuclease (Ape) of hypersensitivity to DNA damage and spontaneous mutator phenotype in *apnl-yeast,*" *Nucleic Acids Research* 23(24):5027-5033, 1995.
Zhou et al., "Novel plant SUN-KASH bridges are involved in RanGAP anchoring and nuclear shape determination," *The Journal of Cell Biology* 196(2):203-211, Jan. 2012.

* cited by examiner

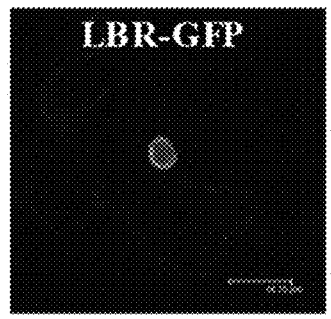
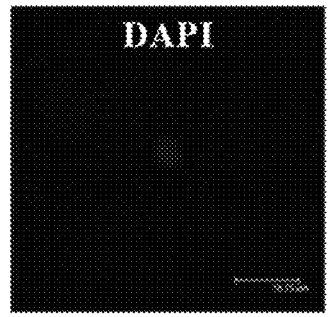
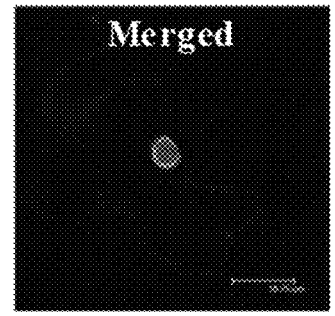
FIG. 3A          FIG. 3B          FIG. 3C
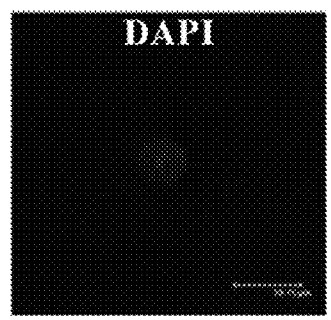
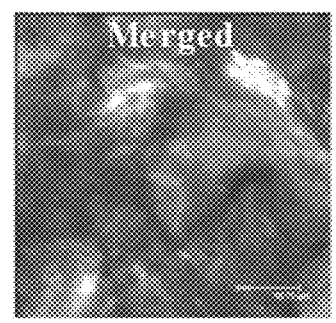
FIG. 3D          FIG. 3E          FIG. 3F
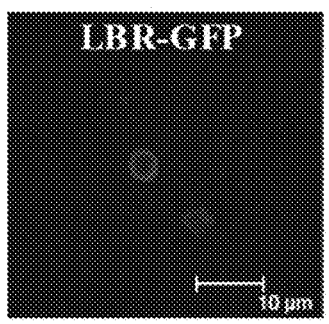
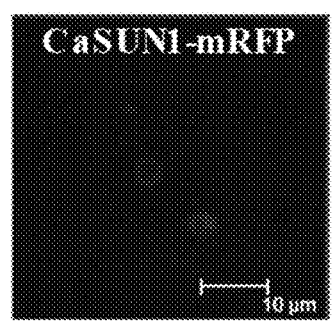
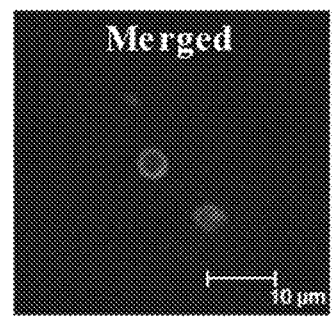
FIG. 3G          FIG. 3H          FIG. 3I

METHOD OF PRODUCING STRESS TOLERANT PLANTS OVEREXPRESSING CASUN1

FIELD OF INVENTION

The present disclosure relates to a method of producing transgenic plants over-expressing CaSUN1 gene. The transgenic plants have enhanced abiotic and biotic stress tolerance. The disclosure also provides cDNA, recombinant DNA constructs, recombinant DNA vectors, and recombinant host cells comprising the CaSUN1 cDNA.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200233_402_SEQUENCE_LISTING.txt. The text file is 8.3 KB, was created on Jan. 1, 2015, and is being submitted electronically via EFS-Web.

BACKGROUND OF THE INVENTION

Water-deficit or dehydration is considered to be a predominant environmental stress and is often associated with other stresses viz., salinity, high temperature, and nutritional deficiencies. Plants, being sessile, have evolved distinct mechanisms to sense such adverse conditions and initiate defense responses. During the past decade, the physiological and molecular basis for plant responses to dehydration tolerance has been the subject of priority research (Krasensky et al., *J. Exp. Bot.*, 2012, 63, 1593-1608; Lawlor et al., *J. Exp. Bot.*, 2013, 64, 83-108). Most of the earlier understanding of cellular responses to dehydration came from gene expression studies (Matsui et al., *Plant Cell Physiol*, 2008, 49, 1135-1149; Shinozaki et al., *J. Exp. Bot.*, 2007, 58, 221-227)

Although such strategies allow identification of stress-responsive genes, they do not necessarily reflect the actual dynamics of final gene products, the proteins (Dumas-Gaudot et al., *Proteomics*, 2004, 4, 451-453). Proteomic analysis offers an opportunity to catalog temporal patterns of protein accumulation during stress perception, adaptation and cell defense (Abdalla et al., *J. Proteomics*, 2012, 75, 2361-2374; Bhushan et al, *J. Proteomics*, 2011, 10, 2027-2046). Further, the level of proteins integrates post-transcriptional and post-translational processing that modulates the quantity, localization and efficiency of the final cell products. This information can hence be included with the annotation of the corresponding gene (Baginsky et al., *J. Exp. Bot.*, 2006, 57, 1485-1491). Thus, identifying novel proteins, determining their expression patterns in dehydration response and understanding their functions would provide the basis for effective engineering strategies to improve crop stress tolerance.

Increasing world-wide demand for staple food products such as rice has put an ever increasing pressure on both agricultural practices and scientific innovation on increasing yield of plants. Concurrently, there has been a demand for sustainable agriculture in the face of increased use of growth stimulants, and vagaries of nature such as water availability or temperature conditions. There is a current pressing need to develop methods, and new varieties of food crops that are better equipped to handle both abiotic and biotic stress factors.

SUMMARY OF INVENTION

In an aspect of the present disclosure, there is provided a recombinant DNA construct comprising of a promoter operably linked to a stress tolerance gene, wherein the stress tolerance gene encodes a polypeptide having amino acid sequence as set forth in SEQ ID NO: 1.

In an aspect of the present disclosure, there is provided a recombinant DNA vector comprising a recombinant DNA construct comprising of a promoter operably linked to a stress tolerance gene, wherein the stress tolerance gene encodes a polypeptide having amino acid sequence as set forth in SEQ ID NO: 1.

In an aspect of the present disclosure, there is provided a recombinant host cell comprising of a recombinant DNA construct comprising of a promoter operably linked to a stress tolerance gene, wherein the stress tolerance gene encodes a polypeptide having amino acid sequence as set forth in SEQ ID NO: 1.

In an aspect of the present disclosure, there is provided a cDNA encoding a polypeptide having amino acid sequence as set forth in SEQ ID NO: 1.

In an aspect of the present disclosure, there is provided a method of producing a transgenic plant with enhanced tolerance to stress, said method comprising: (a) transforming plant cells with recombinant host cells comprising a recombinant DNA construct comprising of a promoter operably linked to a stress tolerance gene, wherein the stress tolerance gene encodes a polypeptide having amino acid sequence as set forth in SEQ ID NO: 1, (b) selecting a transgenic plant cell comprising the recombinant DNA construct from (a), and (c) developing a transgenic plant which shows enhanced tolerance to stress.

In an aspect of the present disclosure, there is provided a transgenic plant or parts thereof including seeds, and progeny that exhibit enhanced stress tolerance, wherein the transgenic plant or part thereof including seeds, and progeny encode in its nuclear genome a recombinant DNA construct comprising of a promoter operably linked to a stress tolerance gene, wherein the stress tolerance gene encodes a polypeptide having amino acid sequence as set forth in SEQ ID NO: 1.

These and other features, aspects and advantages of the present subject matter will be better understood with reference to the following description and appended claims. This summary is provided to introduce a selection of concepts. This summary is not intended to identify key features or essential features of the claimed subject matter, nor is it intended to be used for to limiting the scope of the claimed subject matter.

BRIEF DESCRIPTION OF ACCOMPANYING DRAWINGS

The patent or application file contains at least one drawing executed in color. Copies of this patent or patent application publication with color drawing(s) will be provided by the Office upon request and payment of the necessary fee.

The following drawings form part of the present specification and are included to further illustrate aspects of the present disclosure. The disclosure may be better understood by reference to the drawings in combination with the detailed description of the specific embodiments presented herein.

FIG. 3A-I shows the localization of CaSUN1 in *Nicotiana* epidermal cells, in accordance with an embodiment of the present disclosure.

Figure 4:
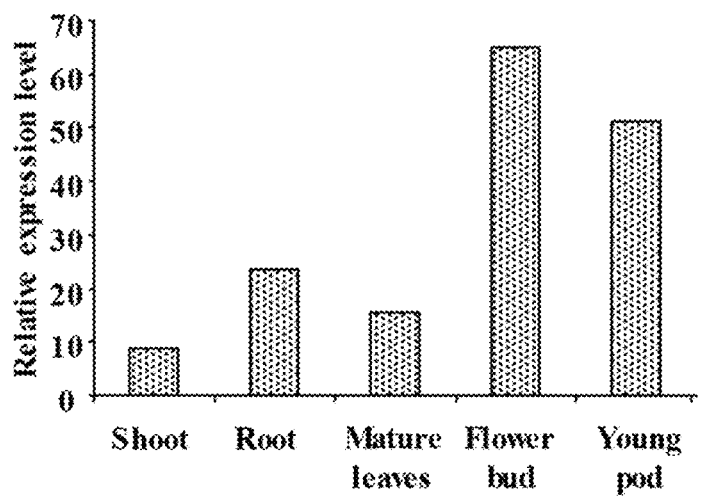

FIG. 4 shows the graphical representation of tissue specific distribution of CaSUN1, in accordance with an embodiment of the present disclosure.

FIG. 5A-D shows the graphical representation of CaSUN1 transcript levels in chickpea seedlings exposed to stress, in accordance with an embodiment of the present disclosure.

Figure 6A:
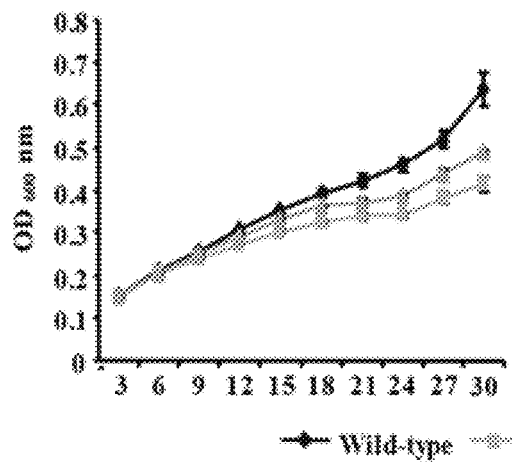
Figure 6B:
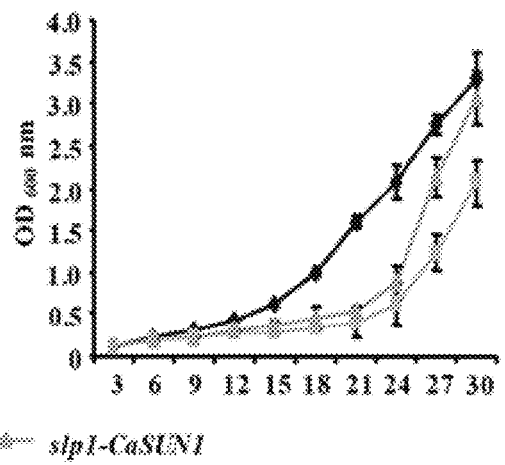
Figure 6C:
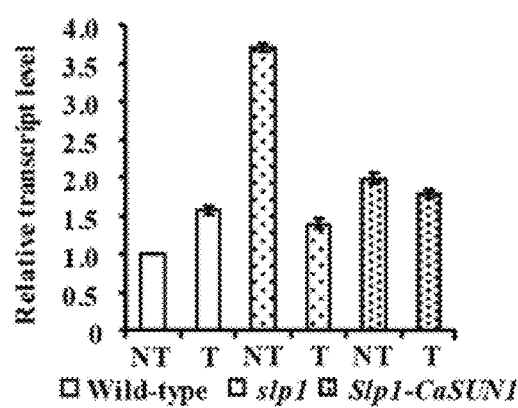

FIG. 6A-C shows the effect of CaSUN1 on growth of Δslp1 yeast strain, in accordance with an embodiment of the present disclosure.

Figure 7:
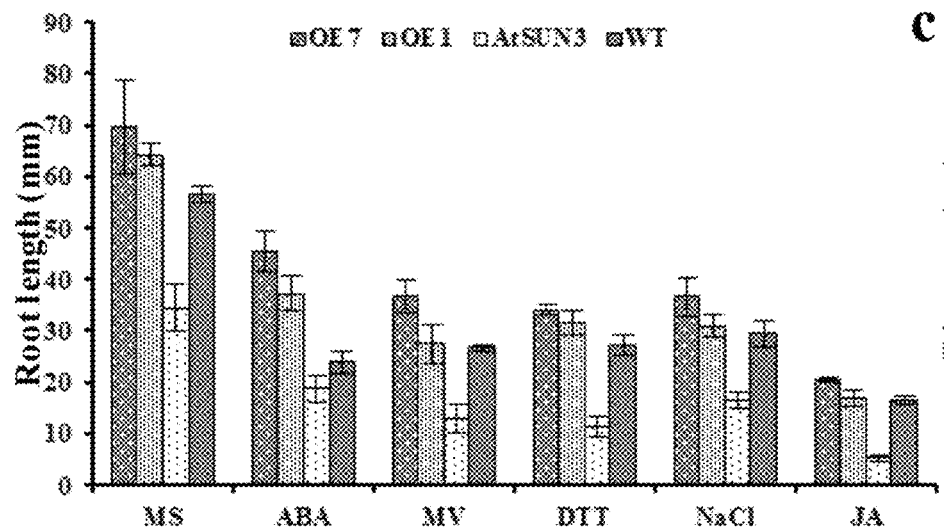

FIG. 7 shows the effect of CaSUN1 over-expression in *arabidopsis* on root length in response to stress, in accordance with an embodiment of the present disclosure.

Figure 8:
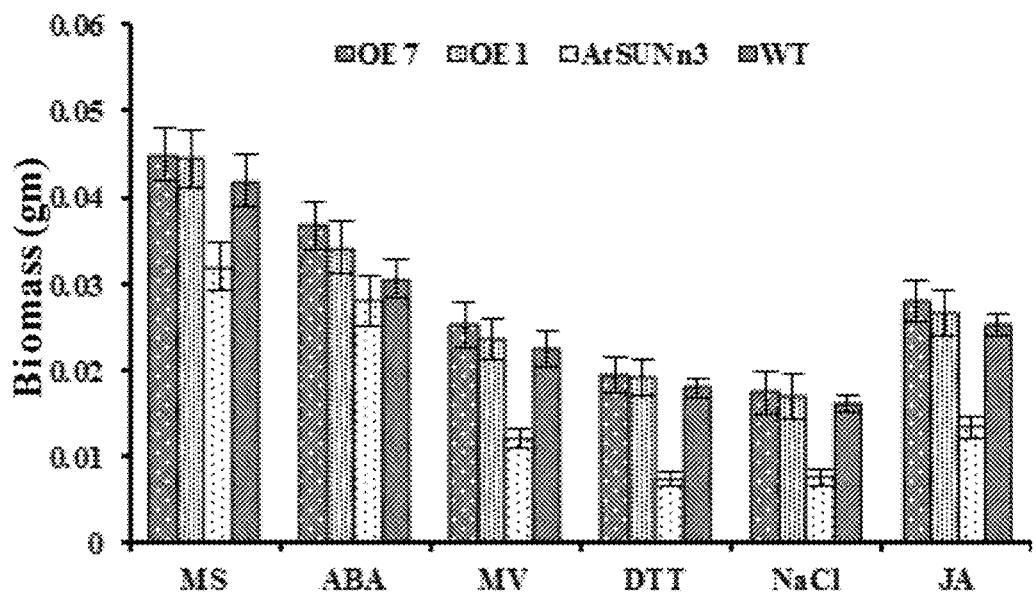

FIG. 8 shows the effect of CaSUN1 over-expression in *arabidopsis* on biomass in response to stress, in accordance with an embodiment of the present disclosure.

Figure 9A:
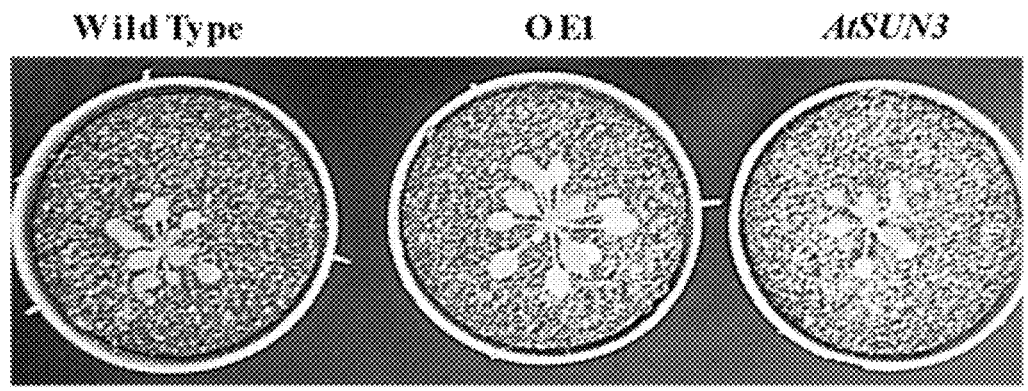
Figure 9B:
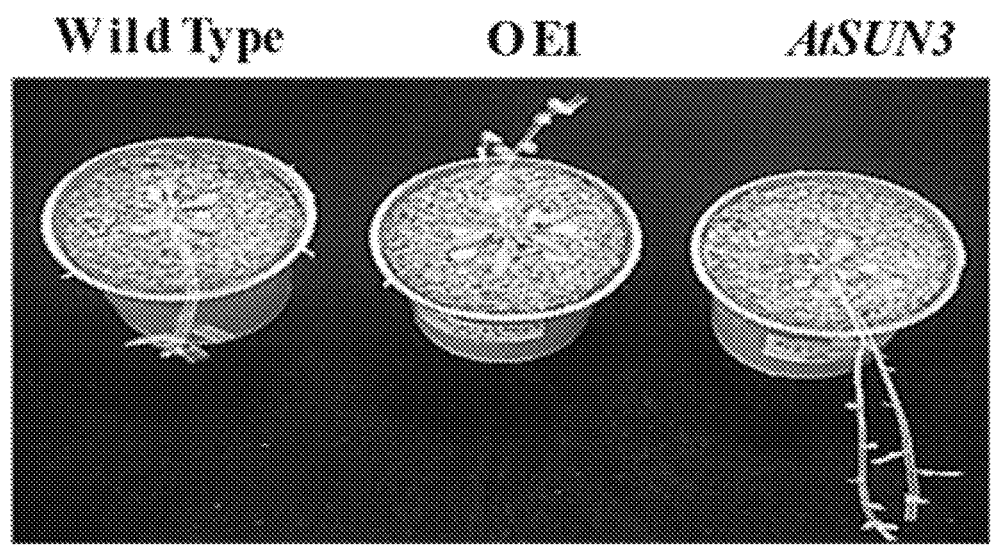

FIG. 9A-B shows the effect of CaSUN1 over-expression in *arabidopsis* in response to dehydration, in accordance with an embodiment of the present disclosure.

DETAILED DESCRIPTION OF THE INVENTION

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of such steps or features.

Definitions

For convenience, before further description of the present invention, certain terms employed in the specification, example and appended claims are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only.

Throughout this specification, unless the context requires otherwise the word "comprise", and variations such as "comprises" and "comprising", will be understood to imply the inclusion of a stated element or step or group of element or steps but not the exclusion of any other element or step or group of element or steps. The term "including" is used to mean "including but not limited to". "Including" and "including but not limited to" are used interchangeably.

"Primers" are synthesized nucleic acids that anneal to a complementary target DNA strand by hybridization to form a hybrid between the primer and the target DNA strand, and then extended along the target DNA strand by polymerase activity, e.g., a DNA polymerase. Primer pairs described in the present invention refer to their use for amplification of a target nucleic acid sequence, e.g., by polymerase chain reaction or other conventional nucleic-acid amplification methods.

The term "genetic transformation" refers to a process of introducing a DNA sequence or construct (e.g., a vector or expression cassette) into a cell in which that exogenous DNA is incorporated into a chromosome or is capable of autonomous replication.

The term "transgenic" refers to a cell contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene.

The term "transgene" refers to any nucleic acid sequence which is introduced into the genome of a cell by experimental manipulations. A transgene may be an "endogenous DNA sequence," or a "heterologous DNA sequence" (i.e., "foreign DNA"). A transgene is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

The term "vector" refers to a DNA molecule capable of replication in a host cell and/or to which another DNA segment can be operably linked so as to bring about replication of the attached segment. A plasmid is an exemplary vector.

The term "expression vector" refers to a vector comprising an expression cassette.

The term "polypeptide" and "peptide are used interchangeably for the purposes of the present disclosure.

The term "transformed cell" refers to a cell, the DNA complement of which has been altered by the introduction of an exogenous DNA molecule into that cell.

The term "transgenic plant" refers to a plant or progeny plant of any subsequent generation derived therefrom, wherein the DNA of the plant or progeny thereof contains an introduced exogenous DNA segment not originally present in a non-transgenic plant of the same strain. The transgenic plant may additionally contain sequences which are native to the plant being transformed, but wherein the "exogenous" gene has been altered in order to alter the level or pattern of expression of the gene.

The term "polynucleotide" used in the present invention refers to a DNA polymer composed of multiple nucleotides chemically bonded by a series of ester linkages between the phosphoryl group of one nucleotide and the hydroxyl group of the sugar in the adjacent nucleotide.

SEQ ID NO: 1 shows the amino acid sequence of CaSUN1.

SEQ ID NO: 2 shows the polynucleotide sequence of CaSUN1.

SEQ ID NO: 3 shows the forward primer for cloning CaSUN1.

SEQ ID NO: 4 shows the reverse primer for cloning CaSUN1.

In an embodiment of the present disclosure, there is provided a recombinant DNA construct comprising of a promoter operably linked to a stress tolerance gene, wherein the stress tolerance gene encodes a polypeptide having amino acid sequence as set forth in SEQ ID NO: 1.

In an embodiment of the present disclosure, there is provided a recombinant DNA construct comprising of a promoter operably linked to a stress tolerance gene, wherein the stress tolerance gene has a polynucleotide sequence as set forth in SEQ ID NO: 2.

In an embodiment of the present disclosure, the promoter is selected from the group consisting of pUbi, CaMV 35S, opine promoters, Adh-1, and Act-1.

In a preferred embodiment of the present disclosure, the promoter is CaMV 35S.

In an embodiment of the present disclosure, there is provided a recombinant DNA construct comprising of a promoter operably linked to a stress tolerance gene, wherein the stress tolerance gene encodes a polypeptide having amino acid sequence as set forth in SEQ ID NO: 1.

In an embodiment of the present disclosure, there is provided a recombinant DNA vector comprising a recombinant DNA construct comprising of a promoter operably linked to a stress tolerance gene, wherein the stress tolerance gene has a polynucleotide sequence as set forth in SEQ ID NO: 2.

In an embodiment of the present disclosure, there is provided a recombinant host cell comprising of a recombinant DNA vector comprising of a recombinant DNA construct comprising of a promoter operably linked to a stress tolerance gene, wherein the stress tolerance gene encodes a polypeptide having amino acid sequence as set forth in SEQ ID NO: 1.

In an embodiment of the present disclosure, there is provided a recombinant host cell comprising of a recombinant DNA vector comprising of a recombinant DNA construct comprising of a promoter operably linked to a stress tolerance gene, wherein the stress tolerance gene has a polynucleotide sequence as set forth in SEQ ID NO: 2.

In an embodiment of the present disclosure, the recombinant host cell is a plant cell.

In an embodiment of the present disclosure, the recombinant host cell is an animal cell.

In an embodiment of the present disclosure, the recombinant host cell is a fungal cell.

In an embodiment of the present disclosure, the recombinant host cell is a bacterial cell.

In an embodiment of the present disclosure, the recombinant host cell is *Agrobacterium tumefaciens*.

In an embodiment of the present disclosure, there is provided a cDNA encoding a polypeptide having amino acid sequence as set forth in SEQ ID NO: 1.

In an embodiment of the present disclosure, there is provided a cDNA having polynucleotide sequence as set forth in SEQ ID NO: 2.

In an embodiment of the present disclosure, there is provided a cDNA, wherein expression of the cDNA in cells enhances tolerance against stress, wherein the stress is selected from the group consisting of, salt stress, thermal stress, dehydration stress, and salicylic acid stress.

In an embodiment of the present disclosure, there is provided a method of producing a transgenic plant with enhanced tolerance to stress, said method comprising of (a) transforming plant cells with host cells comprising of a recombinant DNA vector comprising of a recombinant DNA construct comprising of a promoter operably linked to a stress tolerance gene encoding a polypeptide having amino acid sequence as set forth in SEQ ID NO: 1, (b) selecting a transgenic plant comprising the recombinant DNA construct from (a), and (c) developing a transgenic plant which shows enhanced tolerance to stress.

In an embodiment of the present disclosure, the stress is selected from the group consisting of dehydration stress, salt stress, salicylic acid stress, and thermal stress.

In an embodiment of the present disclosure, the method of transformation is selected from the group consisting of *Agrobacterium* mediated transformation, biolistics, electroporation, protoplast fusion, and liposome mediated transformation.

In a preferred embodiment of the present disclosure, the method of transformation is *Agrobacterium* mediated transformation.

In an embodiment of the present disclosure, there is provided a transgenic plant or parts thereof, including seeds, and progeny that express a polypeptide having amino acid sequence as set forth in SEQ ID NO: 1.

In an embodiment of the present disclosure, there is provided a transgenic plant or parts thereof, including seeds, and progeny that express a polypeptide encoded by a polynucleotide sequence as set forth in SEQ ID NO: 2.

In an embodiment of the present disclosure, there is provided a transgenic plant or parts thereof, including seeds, and progeny that express a polypeptide having amino acid sequence as set forth in SEQ ID NO: 1, wherein the transgenic plant or parts thereof, including seeds, and progeny is a monocot.

In an embodiment of the present disclosure, the monocot is selected from the group consisting of corn, rice, wheat, rye, millet, and banana.

In an embodiment of the present disclosure, there is provided a transgenic plant or parts thereof, including seeds, and progeny that express a polypeptide having amino acid sequence as set forth in SEQ ID NO: 1, wherein the transgenic plant or parts thereof, including seeds, and progeny is a dicot.

In an embodiment of the present disclosure, the dicot is selected from the group consisting of beans, peas, potato, eggplant, peppers, squash, melons, coffee, citrus, broccoli, turnips, legumes, yams, *arabidopsis*, and apples.

In an embodiment of the present disclosure, there is provided a transgenic plant or part thereof including seeds, and progeny that show enhanced tolerance to salt stress.

In an embodiment of the present disclosure, there is provided a transgenic plant or part thereof including seeds, and progeny that show enhanced tolerance to thermal stress.

In a preferred embodiment of the present disclosure, there is provided a transgenic plant or part thereof including seeds, and progeny that show enhanced tolerance to cold stress.

In an embodiment of the present disclosure, there is provided a transgenic plant or part thereof including seeds, and progeny that show enhanced tolerance to dehydration induced stress.

In an embodiment of the present disclosure, there is provided a transgenic plant or part thereof including seeds, and progeny that show enhanced tolerance to salicylic acid induced stress.

In an embodiment of the present disclosure, there is provided a transgenic plant or part thereof including seeds, and progeny that show enhanced tolerance to salt stress, thermal stress, dehydration induced stress, and salicylic acid induced stress.

In a preferred embodiment of the present disclosure, the dicot transgenic plant or part thereof including seeds that shows enhanced tolerance to stress is *Arabidopsis*.

In an embodiment of the present disclosure, there is provided a transgenic plant or part thereof including seeds, and progeny that show enhanced tolerance to stress, wherein a recombinant DNA construct comprising of a promoter operably linked to a stress tolerance gene encoding a polypeptide having amino acid sequence as set forth in SEQ ID NO: 1 is nuclear genome encoded.

In embodiment of the present disclosure, there is provided a transgenic plant or part thereof including seeds, and progeny that show enhanced tolerance to stress, wherein a recombinant DNA construct comprising of a promoter operably linked to a stress tolerance gene having a polynucleotide sequence as set forth in SEQ ID NO: 2 is nuclear genome encoded.

In an embodiment of the present disclosure, the polypeptide having amino acid sequence as set forth in SEQ ID NO: 1 is localized to the inner nuclear membrane.

In an embodiment of the present disclosure, the transcript levels of the polypeptide having amino acid sequence as set forth in SEQ ID NO: 1 in a plant cell are downregulated in response to dehydration induced stress.

In an embodiment of the present disclosure, the transcript levels of the polypeptide having amino acid sequence as set forth in SEQ ID NO: 1 in a plant cell are downregulated in response to cold induced stress.

In an embodiment of the present disclosure, the transcript levels of the polypeptide having amino acid sequence as set forth in SEQ ID NO: 1 in a plant cell are downregulated in response to salt induced stress.

In an embodiment of the present disclosure, the transcript levels of the polypeptide having amino acid sequence as set forth in SEQ ID NO: 1 in a plant cell are downregulated in response to salicylic acid induced stress.

In an embodiment of the present disclosure, a polypeptide having amino acid sequence as set forth in SEQ ID NO: 1 is expressed in shoot, root, mature leaves, flower bud, and young pod tissue.

In an embodiment of the present disclosure, a polypeptide having amino acid sequence as set forth in SEQ ID NO: 1 is maximally expressed in flower buds.

In an embodiment of the present disclosure, expression of a polypeptide having amino acid sequence as set forth in SEQ ID NO: 1 in Δslp1 yeast strain rescues the growth defect.

In an embodiment of the present disclosure, over-expression of a polypeptide having amino acid sequence as set forth in SEQ ID NO: 1 in AtSUN3 mutants rescues the root length phenotype of AtSUN3 mutants.

In an embodiment of the present disclosure, over-expression of a polypeptide having amino acid sequence as set forth in SEQ ID NO: 1 in AtSUN3 mutants rescues the biomass phenotype of AtSUN3 mutants.

In an embodiment of the present disclosure, over-expression of a polypeptide having amino acid sequence as set forth in SEQ ID NO: 1 in AtSUN3 mutants rescues the dehydration phenotype of AtSUN3 mutants.

In an embodiment of the present disclosure, over-expression of a polypeptide having amino acid sequence as set forth in SEQ ID NO: 1 in plants results in enhanced stress tolerance.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skills in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary. The example is provided just to illustrate the invention and therefore, should not be construed to limit the scope of the invention.

Example 1: Identification and Down-Regulation of Dehydration Responsive Gene, CaSUN1

Three-week old chickpea seedlings were subjected to progressive dehydration over a period of 120 hours. The membrane associated proteins were extracted from unstressed and stressed seedlings, resolved on to 2D gels, followed by detection by mass spectrometry (MS) and analysis.

The MS/MS analysis identified 95 dehydration-responsive proteins (DRPs), the ion scores of which were statistically significant ($p<0.05$). A candidate protein that was downregulated in response to dehydration showed homology to membrane protein CH1-like, and was putatively given the name CaSUN1.

Figure 1:
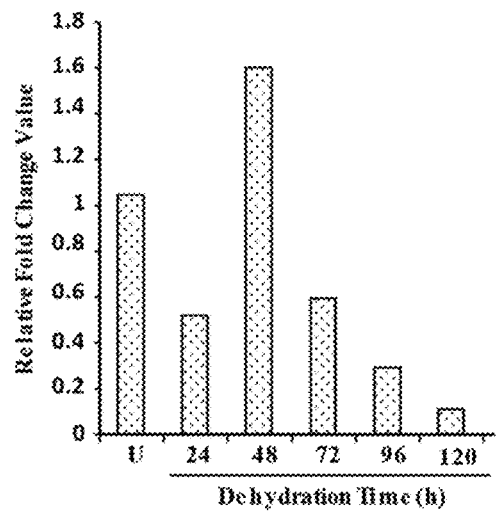
FIG. 1 shows the graphical depiction of down-regulation of CaSUN1 transcript levels in chickpea seedlings, in accordance with an embodiment of the present disclosure.

FIG. 1 shows the transcript levels of CaSUN1 in dehydrated chickpea seedlings. It can be seen that transcript levels of CaSUN1 are decreased by five-fold over a period of 120 hours.

Figure 2:
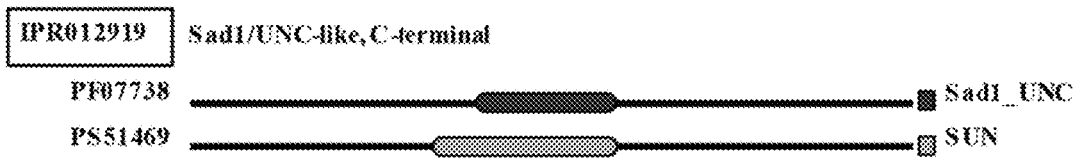
FIG. 2 shows the depiction of genomic organization of CaSUN1, in accordance with an embodiment of the present disclosure.

FIG. 2 shows the genomic organization of CaSUN1. There is a putative SUN domain at mid position. The C-terminal shows homology to Sad1/UNC like.

In-silico analysis of CaSUN1 shows the presence of three transmembrane domains, a coiled-coil region and a secretory signal.

Isolation of CaSUN1, and Sequence Analysis:

The full length cDNA of CaSUN1 was cloned by RACE, using the SMART™ RACE cDNA amplification kit (Clonetech Laboratories).

Example 2: Multi-Organelle Localization of CaSUN1

In-vivo targeting and expression of CaSUN1 was examined in *Nicotiana* epidermal cells using CaSUN1-EYFP and CaSUN1-mRFP fusion proteins. The transient expression was detected by confocal microscopy. The plant nuclear envelope marker, LBR-GFP was used a positive control.

Primers used for the PCR for cloning CaSUN1 are as set forth in SEQ ID NO: 3 and SEQ ID NO: 4. The PCR condition used are outlined in Table 1. Primers were obtained from Sigma. A 50 µl reaction mixture contained 10-50 ng DNA template, 1 µl of 10 µM of each primer, 1 µl of 10 mM dNTPs, 5 µl of 10× Taq buffer and 2.5 units of Taq polymerase.

TABLE 1

| Step | Number of cycles | Temperature (° C.) | Time (sec) |
|---|---|---|---|
| Initial denaturation | 1 | 95 | 240 |
| Denaturation | 30 | 94 | 30 |
| Annealing | | 60 | 60 |
| Extension | | 72 | 120 |

FIG. 3 shows the localization of CaSUN1-EYFP to the nuclear envelope. FIG. 3A-C shows the nuclear envelope localization of the positive control, LBR-GFP. CaSUN1-EYFP expression can also be seen in the endoplasmic reticulum and in small vacuolar membranes suggesting trafficking of synthesized protein to the nuclear envelope (3D-F). Co-localization of CaSUN1-mRFP with LBR-GFP suggests that CaSUN1 is localized to the inner nuclear envelope (3G-I).

The open reading frame of CaSUN1 that lacked the stop codon was PCR amplified and cloned in to the pENTR-D/TOPO vector (Invitrogen). The resultant plasmid pENTR-CaSUN1 was subjected to the LR reaction using destination vector pGWB411, 441, and 454 to produce a binary vector containing the C-terminal FLAG, EYFP, and mRFP tag respectively, under the control of the CaMV 35S promoter. Further, pENTR-CaSUN1 was subjected to the LR reaction using the yeast destination vector pAG426GPD-ccdB-EGFP and pAG426GPD-ccdB-EYFP (Addgene) to produce C-terminal tags under the control of GAP promoter.

Transient Assay of CaSUN1 in *Nicotiana* Leaves:

*A. tumefaciens* strain GV3101 was transformed with the candidate gene construct by freeze-thaw method for transient expression of CaSUN1. The transformed *Agrobacterium* cells were grown at 28° C. in YEP medium supplemented with appropriate antibiotics to an $OD_{600}$ of 0.6-1. The cells were recovered by centrifugation at 500 g for 15 minutes and resuspended in media containing 10% sucrose, 10 mM $MgCl_2$, 2.6 mM MES (pH 5.8), and 150 mM acetosyringone. Cells were incubated in this medium for at least three hours and infiltrated in to four-week old tobacco leaves. The images were taken 2-3 days after infiltration.

Example 3: Tissue Specific Expression of CaSUN1

FIG. 4 shows the graphical representation of tissue specific expression of CaSUN1 in chickpea seedlings. While CaSUN1 transcripts could be detected in all tissue types such as shoot, root, mature leaves, flower bud, and young bud, maximal transcript level was detected in flower buds, which was over six-fold more than in shoots which had the least expression levels.

Example 4: Stress-Responsive Transcriptional Regulation of CaSUN1

Figure 5A:
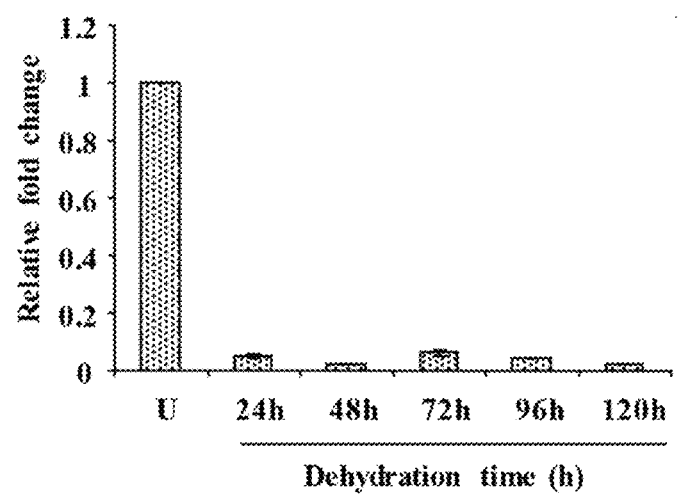

Transcript levels of CaSUN1 in chickpea seedlings were quantified under dehydration conditions using quantitative real time-polymerase chain reaction (q RT-PCR). Primers used for detection of CaSUN1 transcript is as set forth in SEQ ID NO: 3 (forward) and SEQ ID NO: 4 (reverse). FIG. 5A shows that transcript levels of CaSUN1 at various time intervals post-dehydration. It can be seen that there is a severe and significant decrease in CaSUN1 transcript levels as early as 24 hours post dehydration. There is approximately more than a nine-fold decrease by 24 hours compared to controls.

Figure 5B:
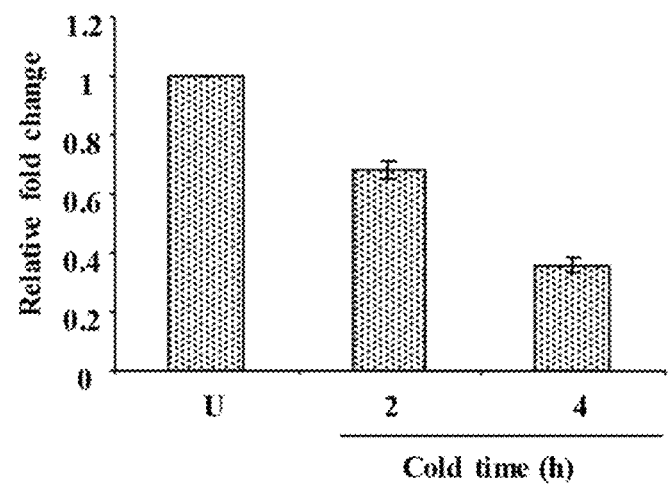

FIG. 5B shows the transcript levels of CaSUN1 at various time intervals in response to cold stress. It can be seen that, in response to cold stress, transcript levels of CaSUN1 are reduced by approximately 50% by four hours post cold stress with respect to controls.

Figure 5C:
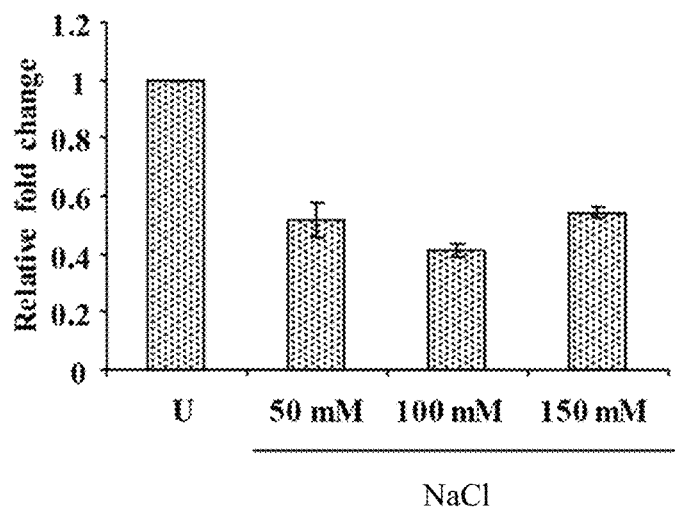

FIG. 5C shows the transcript levels of CaSUN1 in response to varying concentration of salt in a test for salt stress. It can be seen that at salt concentrations ranging from 50 mM-150 mM, transcript levels of CaSUN1 are reduced by approximately 50% compared to controls.

Figure 5D:
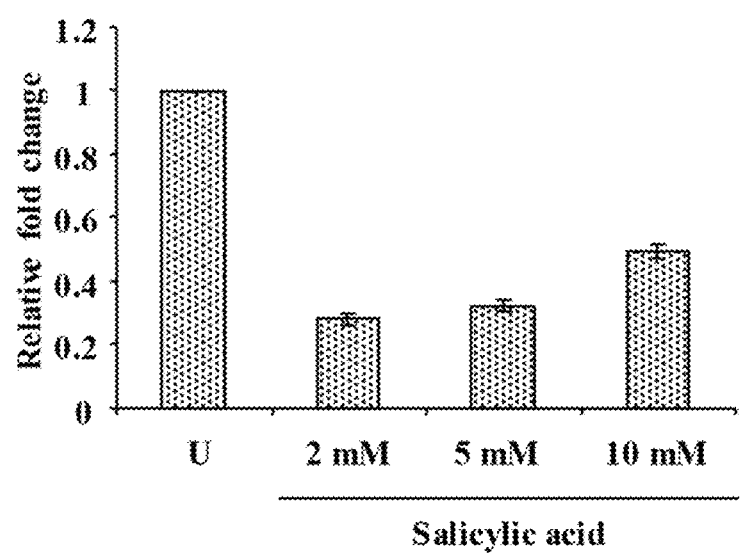

To examine whether CaSUN1 is responsive to pathogen infection/biotic stress, chickpea seedlings were treated with salicylic acid as such compounds are reported to mimic pathostress response (Clarke et al., *Plant Cell*, 2000, 12, 2175-2190). FIG. 5D shows the transcript levels of CaSUN1 in response to salicylic acid. It can be seen that CaSUN1 transcript levels are suppressed by 50%-70% upon salicylic acid treatment ranging from 2 mM-10 mM. A general trend of salicylic acid mediated CaSUN1 suppression can be seen in chickpea seedlings.

qRT-PCR:

Total RNA was isolated either using the RNeasy Plant Mini kit (Qiagen) or the TriPure reagent (Invitrogen). cDNA was prepared using SuperScript® VILO™ cDNA Synthesis Kit (Invitrogen) according to manufacturer's instructions. The qRT-PCR assays were performed with the ABI PRISM 7700 sequence detection system (Applied Biosystems) using SYBR Green PCR Master mix in a final volume of 20 µL including cDNA template and appropriate primer pairs. The internal standards EFla and ACTJ were used for normalizing the qRT-PCR data.

Growth Conditions and Stress Treatment:

The seedlings were grown in pots (10-12 seedlings/1.5 L capacity pots with 18 cm diameter) containing a mixture of soil and soilrite (2:1 w/w ratio) in an environmentally controlled growth room and maintained at 25±2° C., 50±5% relative humidity under 16 hours photoperiod (270 µmol/m$^2$/second light intensity). A gradual dehydration condition was applied on three-week old seedlings by withdrawing water for a period of 120 hours. In a separate experiment, seedlings were also subjected to other stresses such as varying NaCl concentrations (100, 250, and 500 mM), and low temperature (4° C.). Different concentrations of ABA (25, 50, and 100 µM), methyl viologen (50, 100 µM), and salicylic acid (2, 5, and 10 mM) were applied by spraying the respective solutions on the seedlings. The tissues were harvested, flash frozen in liquid nitrogen, and stored at −80° C.

Example 5: Functional Complementation of Yeast slp1 Mutant by CaSUN1 slp1 mutants are hypersensitive to stress inducers that activate the unfolded protein response pathway (UPR). To ascertain the functional role of CaSUN1 in ER stress response, the slp1 mutant was transformed with the yeast expression vector, pYES2, in which CaSUN1 was cloned under the transcriptional control of GAL promoter.

FIG. 6A, B show that expression of CaSUN1 in slp1 mutant yeast background significantly restored the growth defect of slp1 mutant yeast strain. This suggests that CaSUN1 may have a functional regulatory role in mediating the activation of the intracellular stress response pathway.

KAR2 is a molecular chaperone and indicator of UPR stress in yeast. FIG. 6C shows the transcript levels of CaSUN1 in slp1 yeast mutant background in response to DTT treatment, which is a known inducer of UPR stress. It can be seen that expression of CaSUN1 ameliorates KAR2 expression suggesting that CaSUN1 may be functional in-vivo in protecting yeast cells from UPR stress, and that the phenotypic complementation is due to CaSUN1.

Yeast Transformation and Complementation Assay:

The pYES2 vector (Invitrogen) was constructed with CaSUN1 cDNA via BamHI/XhoI to generate plasmid pYES2-CaSUN1 for complementation assay. The slp1 mutant (FY; Mat α; ura3-52; HIS3; leu2Δ1; LYS2; TRP1; YOR154w(4,1762)::kanMX4) and wild-type strains (Mat α; ura3-52; HIS3; leu2Δ1; TRP1; GAL2) were obtained from EUROSCARF. Wild-type or mutant yeast cells were transformed with plasmids pYES2-CaSUN1 or the empty vector pYES2. Yeast transformation was performed using the lithium acetate method (Geno Technology Inc.) and selected on SD-Ura (Invitrogen) by growing the cells at 30° C. for 3-4 days. The respective strains were grown in SD-Ura (non-inducible) and SD-Gal/Raf-URA (inducible) media. The overnight grown cultures were diluted to $OD_{600}$~0.1 in the respective medium containing 2 mM DTT. The growth was monitored every three hours by measuring the $OD_{600}$ of the cultures.

Example 6: Over-Expression of CaSUN1 in *Arabidopsis* Enhances Stress Tolerance

Transgenic *Arabidopsis* were developed in which CaSUN1 is constitutively over-expressed under the control of CaMV 35S promoter. No phenotypic abnormalities were observed in unstressed conditions in at least two transgenic lines, designated OE-1, and OE-2.

OE-1 and OE-2 were subjected to various stress conditions such as salt exposure, DTT treatment, oxidative stress, and JA.

FIG. 7 shows the effect of various stressors in OE-1 and OE-2 transgenic plants compared to AtSUN1 mutant and control plants with respect to root length. It can be seen that over-expression of CaSUN1 rescues the defects seen in both AtSUN1 mutants and wild-type *arabidopsis* exposed to various stressors, and in many cases enhances the protective effect of CaSUN1 over-expression, suggesting that CaSUN1 may have a role in regulating plant growth and health in response to stress.

FIG. 8 shows the effect of various stressors in OE-1 and OE-2 transgenic plants compared to AtSUN1 mutant and control plants with respect to biomass. It can be seen that over-expression of CaSUN1 rescues the defect seen in AtSUN1 mutants with regard to biomass, suggesting that CaSUN1 may have a role in regulating plant growth and yield in response to stress.

The sensitivity of wild type and AtSUN1 plants and OE-1 was also compared in response to dehydration treatment (18 days) of four-week old plants. FIG. 9 shows that while wild type and mutants show wilting, OE-1 transgenic plant shows better adaptation.

Overall, OE-1 plants are more tolerant to multivariate stresses than their wild-type counterparts. Additionally, the transgenic seedlings showed similar phenotypes as that of wild-type seedlings when assayed for germination rate in the presence or absence of exogenously applied ABA.

Genetic Transformation of *Arabidopsis*:

The CaSUN1 constructs were transformed in to *Agrobacterium tumefaciens* GV3101 cells, which were used to transform *Arabidopsis* by floral dip method (Clough et al., *Plant J.*, 1998, 16, 735-743). Putative transgenic seedlings were selected on MS medium containing 50 mg/L kanamycin. For stress treatment, seeds of wild-type and transgenic plants were sterilized, stratified at 4° C. for 72 hours and then grown on MS plates. Seeds were also kept onto identical plates supplemented with DTT (1 mM or 2.5 mM), MV (2 μM or 8 μM), ABA (0.5 μM or 2 μM), NaCl (50 mM or 100 mM), and JA (2 μM or 8 μM).

Overall, the present specification provides transgenic plants and reagents, including cDNA fragments, DNA constructs, DNA vectors, and host cells that are useful in developing said transgenic plants that exhibit enhanced tolerance to stressors such as salt stress, thermal stress, dehydration stress, and salicylic acid stress, and combinations thereof. Such plants are beneficial as they provide resistance against various stress factors that otherwise can be detrimental to the health and development of said plant, especially plants that are of nutritional use for agriculture.

We claim:

1. A recombinant DNA construct comprising a heterologous promoter operably linked to a stress tolerance gene, wherein the stress tolerance gene encodes a polypeptide having an amino acid sequence comprising the full-length of SEQ ID NO: 1.

2. The recombinant DNA construct as claimed in claim 1, wherein the stress tolerance gene has a polynucleotide sequence comprising the full-length of SEQ ID NO: 2.

3. The recombinant DNA construct as claimed in claim 1, wherein the promoter is selected from the group consisting of pUbi, CaMV 35S, Act-1, Adh-1, and opine promoters.

4. A recombinant DNA vector comprising the recombinant DNA construct as claimed in claim 1.

5. A recombinant host cell comprising the recombinant DNA construct as claimed in claim 1 or a recombinant DNA vector that comprises the recombinant DNA construct.

6. The recombinant host cell as claimed in claim 5, wherein the host cell is selected from the group consisting of a plant cell, an animal cell, a fungal cell, and a bacterial cell.

7. A cDNA encoding a polypeptide having an amino acid sequence comprising the full-length of SEQ ID NO: 1.

8. The cDNA as claimed in claim 7, wherein the cDNA has a polynucleotide sequence comprising the full-length of SEQ ID NO: 2.

9. The cDNA as claimed in claim 7, wherein expression of the polypeptide encoded by the cDNA in plant cells enhances tolerance against a stress selected from the group consisting of salt stress, thermal stress, dehydration stress, salicylic acid stress, and combinations thereof.

10. A method of producing a transgenic plant with enhanced tolerance to stress, said method comprising:
   a. transforming plant cells with host cells comprising a recombinant DNA construct comprising a promoter operably linked to a stress tolerance gene, wherein the stress tolerance gene encodes a polypeptide having an amino acid sequence comprising the full-length of SEQ ID NO: 1;
   b. selecting a transgenic plant cell comprising the recombinant DNA construct; and
   c. developing a transgenic plant that shows enhanced tolerance to a stress selected from the group consisting of salt stress, thermal stress, dehydration stress, salicylic acid stress, and combinations thereof.

11. The method as claimed in claim 10, wherein the transgenic plant is a moncot or a dicot.

12. The method as claimed in claim 11, wherein the transgenic plant is selected from the group consisting of corn, rice, wheat, rye, millet, banana, beans, peas, potato, eggplant, peppers, squash, melons, coffee, citrus, broccoli, turnips, legumes, yams, *Arabidopsis*, and apples.

13. A transgenic plant or parts thereof including seeds, and progeny, wherein the transgenic plant or part thereof including seeds, and progeny exhibit enhanced stress tolerance and comprise in its nuclear genome the recombinant DNA construct as claimed in claim 1, wherein the stress is selected from the group consisting of salt stress, thermal stress, dehydration stress, salicylic acid stress, and combinations thereof.

14. The transgenic plant or parts thereof including seeds, and progeny as claimed in claim 13, wherein the transgenic plant or parts thereof including seeds, and progeny is a monocot or a dicot.

15. The transgenic plant or parts thereof including seeds, and progeny as claimed in claim 14, wherein the transgenic plant or parts thereof including seeds, and progeny is selected from the group consisting of corn, rice, wheat, rye, millet, banana, beans, peas, potato, eggplant, peppers, squash, melons, coffee, citrus, broccoli, turnips, legumes, yams, *Arabidopsis*, and apples.

16. A method for producing a transgenic plant that is tolerant to stress, comprising:
   a. introducing into plant cells a cDNA encoding a polypeptide having an amino acid sequence comprising the full-length of SEQ ID NO: 1 or a recombinant DNA construct comprising a promoter operably linked to a stress tolerance gene, wherein the stress tolerance gene encodes a polypeptide having amino acid sequence comprising the full-length of SEQ ID NO: 1;
   b. selecting a transgenic plant cell comprising the cDNA or the recombinant DNA construct; and c. developing a transgenic plant that is tolerant to a stress selected from the group consisting of salt stress, thermal stress, dehydration stress, salicylic acid stress, and combinations thereof, wherein said transgenic plant is a monocot or a dicot selected from the group consisting of corn, rice, wheat, rye, millet, banana, beans, peas, potato, eggplant, peppers, squash, melons, coffee, citrus, broccoli, turnips, legumes, yams, *Arabidopsis*, tobacco, and apples.

* * * * *

SEQUENCE LISTING

<160> NUMBER OF SEQ ID NOS: 4

<210> SEQ ID NO 1
<211> LENGTH: 602
<212> TYPE: PRT
<213> ORGANISM: Cicer arietinum

<400> SEQUENCE: 1

Met Gln Arg Ser Arg Lys Ala Leu Leu Glu Arg Arg Ala Ser Ser Ile
1               5                   10                  15

Lys Thr Ser Ser Ser Val Asn Asn Asn His Phe Tyr Glu Val Ser Leu
            20                  25                  30

Val Phe Val Leu Trp Gly Leu Leu Phe Leu Phe Ser Leu Trp Ile Ser
        35                  40                  45

Tyr Thr Asp Gly Ser Glu Glu Ile Ser Val Gly Leu Ser Lys Trp Asn
    50                  55                  60

Glu Val Asn Gln Gly Phe Cys Lys Ile Ser Asp Pro Ala Lys Tyr Phe
65                  70                  75                  80

Ile Lys Glu Thr Asp Ala Cys Val Pro Ser Glu Ala Leu Leu Tyr Ser
                85                  90                  95

```
Lys Gly Gly Gly Tyr Glu Ala Asn Gly Phe Val Gly Glu Ser Leu Thr
            100                 105                 110
Ser Arg Glu Ser Asp Asp Tyr Ala Val Pro Gly Asp Cys Asn Lys Glu
        115                 120                 125
Asn Thr Asp Ser Ser Asn Arg Glu Glu His Leu Val Glu Ser Cys Glu
130                 135                 140
Ser Ala Asn Lys Leu Glu Asn Asp Thr Gln Lys Ser Asp Arg Leu Pro
145                 150                 155                 160
Trp Thr Val Pro Leu Gly Leu Asp Glu Phe Lys Ser Thr Ala Ile Ser
                165                 170                 175
Ser Lys Val Lys Ser Gly Thr Gly Gln Ser Gly Ser Val Ile His Arg
            180                 185                 190
Leu Glu Pro Gly Gly Ala Glu Tyr Asn Tyr Ala Ser Ala Ser Lys Gly
        195                 200                 205
Ala Lys Val Leu Gly Ser Asn Lys Glu Ala Lys Gly Ala Ser Asn Ile
210                 215                 220
Leu Ser Arg Asp Lys Asp Lys Tyr Leu Arg Asn Pro Cys Ser Val Glu
225                 230                 235                 240
Glu Lys Phe Val Ile Ile Glu Leu Ser Glu Glu Thr Leu Val Asp Thr
                245                 250                 255
Ile Glu Ile Ala Asn Phe Glu His His Ser Ser Asn Leu Lys Asp Phe
            260                 265                 270
Glu Ile His Gly Ser Leu Ser Phe Pro Thr Asp Val Trp Val Phe Leu
        275                 280                 285
Gly Asn Phe Thr Ala Ser Asn Val Arg His Ala Gln Arg Phe Val Leu
290                 295                 300
Lys Glu Pro Lys Trp Val Arg Tyr Leu Lys Leu Asn Leu Gln Ser His
305                 310                 315                 320
Tyr Gly Ser Glu Phe Tyr Cys Thr Leu Ser Val Val Glu Leu Tyr Gly
                325                 330                 335
Val Asp Ala Val Glu Arg Met Leu Glu Asp Leu Ile Asn Thr Gln Asp
            340                 345                 350
Asn Leu Phe Thr Ser Gly Glu Val Asn Asp Asp Lys Lys Thr Val Phe
        355                 360                 365
Pro His Pro Asp Pro Ala Glu Ser Glu His Val His Gln Asn Thr Val
370                 375                 380
Gly Gly Val Asn Ser Asp Pro Ser Ser Glu Ile Thr Ser Ala Asn His
385                 390                 395                 400
Glu Thr Val Lys Ser Asn Ser Val Pro Asp Pro Ile Glu Glu Ile Arg
                405                 410                 415
Gln Gln Val Gly Arg Met Pro Gly Asp Thr Val Leu Lys Ile Leu Met
            420                 425                 430
Gln Lys Val Arg Ser Leu Asp Leu Asn Leu Phe Val Leu Glu Arg Tyr
        435                 440                 445
Leu Glu Asp Leu Asn Ser Arg Tyr Val Asn Ile Phe Lys Glu Tyr Ser
450                 455                 460
Lys Asp Ile Gly Glu Lys Asp Ile Leu Leu Gln Lys Ile Lys Glu Asp
465                 470                 475                 480
Ile Lys Asn Leu Ile Asp Gln Gln Asp Val Ile Ala Lys Asp Ala Ser
                485                 490                 495
Asp Leu Asn Ser Trp Lys Ser Gln Ala Ser Leu Gln Leu Asp His Leu
            500                 505                 510
Leu Trp Asp Asn Ala Val Leu Arg Phe Glu Val Glu Lys Val Arg Glu
```

```
            515                 520                 525
Lys Gln Val Ser Leu Glu Asn Lys Gly Val Ile Val Phe Leu Leu Cys
    530                 535                 540

Cys Ile Phe Ser Ser Ile Ala Val Leu Trp Leu Ser Leu Glu Ile Ala
545                 550                 555                 560

Lys Asn Val Cys Arg Ala Leu Ile Ser Val Asp Arg Thr Val Tyr Ser
                565                 570                 575

Arg Asn Phe Cys Val Cys Ser Phe Ser Trp Phe Leu Leu Leu Leu Ser
                580                 585                 590

Cys Ile Ile Ile Ile Phe Ile Leu Ser Leu
                595                 600
```

<210> SEQ ID NO 2
<211> LENGTH: 1812
<212> TYPE: DNA
<213> ORGANISM: artificial sequence
<220> FEATURE:
<223> OTHER INFORMATION: cDNA CaSUN1

<400> SEQUENCE: 2

```
atgcagagat cacgtaaagc tcttctggaa agaagagctt cttcaataaa aacttcttcc     60
tctgtaaata caatcattt ttatgaagtt tctttggttt ttgttttgtg gggtttactc    120
ttcctcttca gctatggat cagttacaca gatggatctg aagagatttc agtaggatta    180
tcaaaatgga atgaagttaa ccagggattt tgtaaaatct ctgatcctgc taaatatttt    240
attaaagaaa ctgatgcttg cgtcccgtcc gaggctttat tatactctaa aggtggaggt    300
tatgaggcta atggttttgt tggtgagtca ctcactagta gagaaagtga tgattatgca    360
gtacctggtg attgcaataa agaaaatact gattcttcca atagagaaga gcatttagtt    420
gagagttgtg aatctgccaa caacttgag aatgatactc aaaaatctga tcgcttacct    480
tggactgtgc ctcttggtct tgatgaattc aagagcacgg caatcagttc taaagttaag    540
tctggcactg gtcaatctgg aagcgtaata catagattgg agcctggtgg tgctgaatac    600
aattatgctt cggcatcaaa gggagccaaa gttttaggtt ctaataaaga gccaaaggg    660
gcctctaata tcttaagcag ggacaaagac aagtatcttc gaaatccttg ttctgtggag    720
gagaaatttg tcattataga actttccgaa gaaaccttag ttgatactat agaaatcgct    780
aattttgagc accactcttc caatttgaaa gactttgaaa tccatggaag tctgagcttt    840
ccaacagatg tttgggtttt ccttgggaat tttactgcct caaatgtgag gcatgctcaa    900
aggtttgttc ttaaagaacc aaaatgggtg agatacctaa agttgaatct tcaaagccac    960
tatggttcag aattttattg cactctaagt gttgttgaac tttatggtgt ggatgccgtt   1020
gagagaatgc tggaggattt gataaatact caggacaatc tatttacatc tggagaagtt   1080
aatgatgata agaagacagt atttccccat cctgatccgg ctgagagtga acatgttcat   1140
caaaatactg ttgggggagt caattcggac ccttcttccg aaatcacttc tgccaatcat   1200
gagacggtaa aaagtaatag tgttcctgat ccaattgaag aaatccgtca acaagttggc   1260
aggatgcctg gggatactgt tctgaagatt ctaatgcaga aagttcgttc tctagactta   1320
aatttatttg ttttggagcg gtatttggaa gacttaaact ctagatatgt caatattttc   1380
aaagagtaca gcaaagacat aggagaaaaa gatatacttc tacagaagat caaagaagac   1440
attaagaatc tcattgacca gcaggatgtt atagcaaaag atgctagcga tctcaattct   1500
tggaagtctc aagcttcatt gcagttagat catttacttt gggacaatgc tgttttgagg   1560
```

```
tttgaggttg aaaaggtcag ggagaagcag gtctctttgg aaaacaaggg tgtaattgtg    1620
tttttattat gttgtatttt ttcatcaatt gctgtgttat ggctatcttt ggaaatagct    1680
aagaatgtct gtagagcact aataagtgtt gatagaacag tttactccag gaatttttgt    1740
gtgtgtagct tttcctggtt tttactatta ttgagttgta tcattattat tttcatatta    1800
agtttatgat ag                                                        1812

<210> SEQ ID NO 3
<211> LENGTH: 26
<212> TYPE: DNA
<213> ORGANISM: artificial sequence
<220> FEATURE:
<223> OTHER INFORMATION: CaSUN1 forward primer

<400> SEQUENCE: 3
caccatgcag agatcacgta aagctc                                         26

<210> SEQ ID NO 4
<211> LENGTH: 34
<212> TYPE: DNA
<213> ORGANISM: artificial sequence
<220> FEATURE:
<223> OTHER INFORMATION: CaSUN1 reverse primer

<400> SEQUENCE: 4
ctatcataaa cttaatatga aaataataat gata                                34
```